United States Patent [19]

Adorante et al.

[11] Patent Number: 5,891,911
[45] Date of Patent: Apr. 6, 1999

[54] METHOD FOR REDUCING INTRAOCULAR PRESSURE IN THE MAMMALIAN EYE BY ADMINISTRATION OF CALCIUM CHELATORS

[75] Inventors: Joseph S. Adorante, Irvine; Elizabeth WoldeMussie, Laguna Niguel; Guadalupe Ruiz, Corona, all of Calif.

[73] Assignee: Allergan, Waco, Tex.

[21] Appl. No.: 260,648

[22] Filed: Jul. 28, 1995

[51] Int. Cl.⁶ ................................................ A61K 31/23
[52] U.S. Cl. .......................................... 514/532; 514/912
[58] Field of Search ..................................... 514/532, 912

[56] References Cited

U.S. PATENT DOCUMENTS

| | | |
|---|---|---|
| 3,467,756 | 9/1969 | Stone . |
| 4,197,301 | 4/1980 | Smith et al. . |
| 4,565,821 | 1/1986 | Chiou . |
| 4,886,815 | 12/1989 | Schachar . |
| 5,066,664 | 11/1991 | Poli et al. . |
| 5,091,528 | 2/1992 | Gluchowski . |
| 5,260,059 | 11/1993 | Acott et al. . |
| 5,380,303 | 1/1995 | Holly et al. . |

FOREIGN PATENT DOCUMENTS

| | | |
|---|---|---|
| 0 464 727 | 1/1992 | European Pat. Off. . |
| WO 94/08573 | 4/1994 | WIPO . |

OTHER PUBLICATIONS

Schlaepfer et al, Neurochemical Research, vol. 6, No. 3, 1981, Calcium–Mediated Breakdown of Glial Filaments and Neurofilaments in Rat Optic Nerve and Spinal Cord, pp. 243–255.

Tymianski et al, Neuron, vol. 11, Aug. 1993, Cell–Permanent Ca2– Chelators Reduce Early Excitotoxic and Ischemic Neuronal Injury In Vitro and In Vivo, pp. 221–235.

Robert E. Kennedy, Transactions of the Americal Ophthalmological Society, vol. LXXII, 1974, Further Observations On Atypical Band Keratopathy In Glaucoma Patients, pp. 107–122.

Thomas J. Zimmerman, Annals of Ophthalmology, vol. 11, No. 5, May 1979, Medical Trabeculocanalotomy In Monkeys With Cytochalasin B or EDTA, pp. 795–796.

Anders Bill, Upsala Journal of Medical Sciences, vol. 85, No. 3, 1980, Effects of Na2EDTA and Alpha–Chymotrypsin On Aqueous Humor Outflow conductance in Monkey Eyes.

Bill et al, Investigative Ophthalmology & Visual Science, vol. 19/5, May 1980, Effects of intrcameral Na2EDTA and EGTA on Aqueous Outflow routes in the Monkey Eye, pp. 492–504.

Richard P. Haugland, Molecular Probes; Handbook of Fluorescent Probes and Research Chemicals, 1992–1994; Set 20: Calcium Indicators, Chelators and Inonphores, pp. 113–120.

*Primary Examiner*—Zohreh Fay
*Attorney, Agent, or Firm*—James M. Hoch; Robert J. Baran; Martin A. Voet

[57] ABSTRACT

Pharmaceutical compositions and a method are disclosed for treating glaucoma and/or ocular hypertension in the mammalian eye by administering to the mammalian eye the pharmaceutical composition of the invention which contains as the active ingredient one or more compounds having calcium chelating activity. Examples of calcium chelating agents utilized in the pharmaceutical composition and method of treatment are:

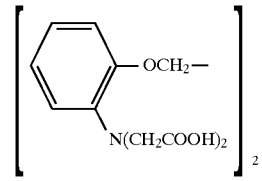

and lower alkyl and alkoxyalkyl esters thereof.

6 Claims, 3 Drawing Sheets

METHOD FOR REDUCING INTRAOCULAR PRESSURE IN THE MAMMALIAN EYE BY ADMINISTRATION OF CALCIUM CHELATORS

BACKGROUND OF INVENTION

1. Field of the Invention

The present invention is directed to pharmaceutical compositions, and primarily to topically applied ophthalmic compositions comprising as the active ingredient one or more compounds having the ability to chelate calcium ions, e.g. intracellular calcium ions. The pharmaceutical compositions are useful for reducing intraocular pressure in animals of the mammalian species. In another aspect, the present invention is directed to administering such formulations and compositions to animals of the mammalian species (including humans) for reducing intraocular pressure in the eye.

2. Brief Description of the Prior Art

Glaucoma is an optical neuropathy associated with elevated intraocular pressures which are too high for normal function of the eye, and results in irreversible loss of visual function. It is estimated in medical science that glaucoma afflicts approximately 2 per cent of the population over the age of forty years, and is therefore a serious health problem. Ocular hypertension, i.e. the condition of elevated intraocular pressure, which has not yet caused irreversible damage, is believed to represent the earliest phase of glaucoma. Many therapeutic agents have been devised and discovered in the prior art for the treatment or amelioration of glaucoma and of the condition of increased intraocular pressure which precedes glaucoma. Other compounds known to be useful in treating intraocular pressure are disclosed in the following patents.

U.S. Pat. No. 3,467,756 describes anti-glaucoma and intraocular hypotensive compositions which contain in an ophthalmic vehicle 10, 11-dihydro-5-(3-methylaminopropyl)-5, 10-epoxy-11-hydroxy-5H-dibenzo [a,d]cycloheptene or related derivatives.

U.S. Pat. No. 4,197,301 describes ophthalmic compositions which contain 1-(4-amino-6,7-dimethoxy-2-quinazolinyl)-4-(2-furanylcarbonyl)piperazine, also known under the name "prazosin".

U.S. Pat. No. 4,565,821 describes a method of topically administering certain dopamine antagonists to reduce ocular hypertension and to treat glaucoma.

U.S. Pat. No. 4,886,815 describes a method for treating retinal edema by administration of dopaminergic antagonists to a patient suffering from such conditions.

U.S. Pat. No. 5,066,664 describes 2-hydroxy-2-alkylphenylamino)-oxazolines and thiazolines as anti-glaucoma and vasoconstrictive agents.

U.S. Pat. No. 5,091,528 describe 6 or 7-(2-imino-2-imidazolidine)-1,4-benzoxazines as α adrenergic agents useful for treating glaucoma.

The foregoing and other anti-glaucoma and ocular hypotensive compounds and agents of the prior art do not provide such treatment or cure for glaucoma and ocular hypertension which is satisfactory in all respects. Therefore, the pharmacological and related arts and sciences continue searching for additional and better anti-glaucoma and ocular hypotensive agents.

1,2-bis(2-aminophenoxy)ethane-N,N,N',N'-tetraacetic acid (BAPTA) is a specific $Ca^{2+}$ chelator that has been used to clamp extracellular $Ca^{2+}$ to desired levels. On the other hand, the acetoxymethyl ester of BAPTA (BAPTA-AM) the uncharged esterified form of the parent compound is used to clamp intracellular $Ca^{2+}(Ca^{2+}i)$. BAPTA-AM penetrates biological cell membranes and is hydrolyzed by intracellular esterases yielding the original charged impermeable form of the compound once again capable of buffering/clamping $Ca^{2+}$. (This is reported in Molecular Probes: Handbook of Fluorescent Probes and Research Chemicals; Richard P. Haugland 1992–1994; Section 20: Calcium Indicators, Chelators and Ionophores, pages 119–128.)

SUMMARY OF THE INVENTION

Surprisingly it has been discovered in accordance with the present invention that calcium chelating agents are effective as anti-glaucoma agents and as agents for reducing intraocular pressure, when such agents are applied to the mammalian eye in a pharmaceutical composition, preferably in a topical ophthalmic composition. Accordingly, the present invention relates to a method of treating glaucoma, or ocular hypertension by topically administering to the mammalian eye an ophthalmic composition which contain an effective amount of a calcium chelating agent. A preferred example of calcium chelating agents suitable as the active ingredients of the ophthalmic compositions of the invention are:

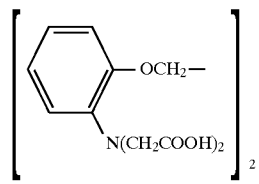

and esters, e.g. the lower alkyl and alkoxyalkyl esters thereof. Such esters may be represented by the general formula

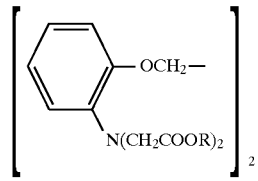

wherein R is lower alkyl, e.g. an alkyl radical having from 1 to 6 carbon atoms, or

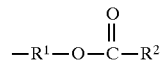

wherein $R^1$ is a lower alkylene radical, e.g. an alkylene radical having from 1 to 6 carbon atoms, and $R^2$ is R, as defined above. R, $R^1$ and $R^2$ may be interrupted with O or N radicals as in alkyloxy alkyl and alkylaminoalkyl moieties, e.g. $R_1$ may be $—CH_2—N(CH_3)CH_2CH_2—$ and $—CH_2—O—CH_2—CH_2—$. Preferably, $R^1$ and $R^2$ will comprise from 1 to 4 carbon atoms, e.g. 1 carbon atom.

While not wishing to be bound by theory it is believed that calcium chelating agents, e.g. 1,2-bis (2-aminophenoxy) ethane-N, N, N',) N'-tetraacetic acid (BAPTA) or the acetoxymethyl ester of BAPTA (BAPTA-AM), are useful for treating hypertensive glaucoma, because intracellular $(Ca^{2+}i)$ is fundamental in the activation/control and modulation of epithelial fluid secretion. Thus, clamping/lowering the level of $Ca^{2+}i$ in the ciliary epithelium, the tissue responsible for aqueous humor formation and a determinant of intraocular pressure (IOP), will reduce inflow and therefore IOP.

The ophthalmic compositions of the invention contain the active ingredient in a concentration range of approximately 0.0001 to 0.1 per cent weight by volume. The composition itself includes, in addition to the active ingredient, such excipients which are per se well known in the art for preparing ophthalmic compositions, particularly ophthalmic solutions. In accordance with the method of the invention the ophthalmic compositions, preferably ophthalmic solutions are applied topically to the mammalian eye approximately 1 or 2 times daily.

DETAILED DESCRIPTION OF THE INVENTION

Figure 1:
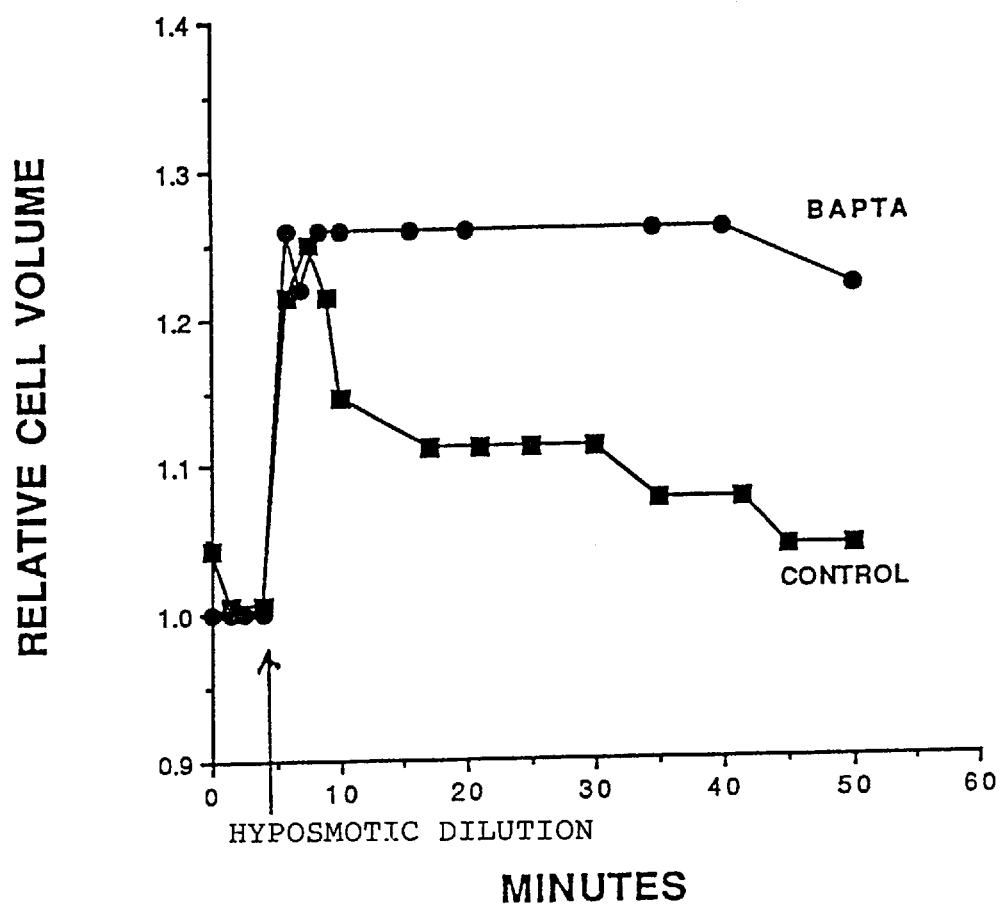
FIG. 1 is a graph showing the effect of topical administration of the drug BAPTA-AM on the regulatory volume decrease (RVD) of a suspension of cultured human non-pigmented ciliary epithelial cells.

The compounds which are utilized in accordance with the method of the present invention, and in the pharmaceutical compositions of the present invention, are calcium chelating agents. In this regard the term calcium chelating agent is defined as those compounds which complex with calcium ions under physiological conditions, e.g. in an aqueous media at a pH of from 6.5 to 7.8. Specific and preferred examples of calcium chelating agents which are utilized in accordance with the present invention are provided below.

For reducing intraocular pressure in a mammalian eye, and particularly for treatment of glaucoma in humans suffering from that condition, the active compounds (or mixtures thereof) are administered in accordance with the present invention to the eye admixed with an ophthalmically acceptable carrier. Any suitable, e.g., conventional, ophthalmically acceptable carrier may be employed. A carrier is ophthalmically acceptable if it has substantially no long term or permanent detrimental effect on the eye to which it is administered. Examples of ophthalmically acceptable carriers include water (distilled or deionized water) saline and other aqueous media. In accordance with the invention, the active compounds are preferably soluble in the carrier which is employed for their administration, so that the active compounds are administered to the eye in the form of a solution. Alternatively, a suspension of the active compound or compounds (thereof) in a suitable carrier may also be employed.

In accordance with the invention the active compounds (or mixtures or salts thereof) are administered in an ophthalmically acceptable carrier in sufficient concentration so as to deliver an effective amount of the active compound or compounds to the eye. Preferably, the ophthalmic, therapeutic solutions contain one or more of the active compounds in a concentration range of approximately 0.0001% to approximately 0.1% (weight by volume) and more preferably approximately 0.0005% to approximately 0.1% (weight by volume).

Any method of administering drugs directly to a mammalian eye may be employed to administer, in accordance with the present invention, the active compound or compounds to the eye to be treated. By the term "administering directly" is meant to exclude those general systemic drug administration modes, e.g., injection directly into the patient's blood vessels, oral administration and the like, which result in the compound or compounds being systemically available. The primary effect on the mammal resulting from the direct administering of the active compound or compounds to the mammal's eye is preferably a reduction in intraocular pressure. More preferably, the active useful compound or compounds are applied topically to the eye or are injected directly into the eye. Particularly useful results are obtained when the compound or compounds are applied topically to the eye in an ophthalmic solution (ocular drops).

Topical ophthalmic preparations, for example ocular drops, gels or creams, are preferred because of ease of application, ease of dose delivery, and fewer systemic side effects, such as cardiovascular hypotentions. An exemplary topical ophthalmic formulation is shown below in Table I. The abbreviation q.s. means a quantity sufficient to effect the result or to make volume.

TABLE I

| Ingredient | Amount (% W/V) |
|---|---|
| Active Compound in accordance with the invention, | about 0.0001 to about 0.1 |
| Preservative | 0–0.10 |
| Vehicle | 0–40 |
| Tonicity Adjustor | 1–10 |
| Buffer | 0.01–10 |
| pH Adjustor | q.s. pH 4.5–7.5 |
| antioxidant | as needed |
| Purified Water | as needed to make 100% |

Various preservatives may be used in the ophthalmic preparation described in Table I above. Preferred preservatives include, but are not limited to, benzalkonium chloride, chlorobutanol, thimerosal, phenylmercuric acetate, and phenylmercuric nitrate. Likewise, various preferred vehicles may be used in such ophthalmic preparation. These vehicles include, but are not limited to, polyvinyl alcohol, povidone, hydroxypropyl methyl cellulose, poloxamers, carboxymethyl cellulose, hydroxyethyl cellulose, and purified water.

Tonicity adjustors may be added as needed or convenient. They include, but are not limited to, salts, particularly sodium chloride, potassium chloride, mannitol, and glycerin, or any other suitable ophthalmically acceptable tonicity adjustor.

Various buffers and means for adjusting pH may be used so long as the resulting preparation is ophthalmically acceptable. Accordingly, buffers include but are not limited to, acetate buffers, citrate buffers, phosphate buffers, and borate buffers. Acids or bases may be used to adjust the pH of these formulations as needed.

In a similar vein, ophthalmically acceptable antioxidants include, but are not limited to, sodium metabisulfite, sodium thiosulfate, acetylcysteine, butylated hydroxyanisole, and butylated hydroxytoluene.

The ophthalmic solution (ocular drops) may be administered to the mammalian eye as often as necessary to maintain an acceptable level of intraocular pressure in the eye. In other words, the ophthalmic solution (or other formulation) which contains the calcium chelating agent as the active ingredient, is administered to the mammalian eye as often as necessary to maintain the beneficial hypotensive effect of the active ingredient in the eye. Those skilled in the art will recognize that the frequency of administration depends on the precise nature of the active ingredient and its concentration in the ophthalmic formulation. Within these guidelines it is contemplated that the ophthalmic formulation of the present invention will be administered to the mammalian eye approximately once or twice daily.

Specific examples of calcium chelating agents which are used as the active effective ingredients in the ophthalmic compositions of the present invention are described and shown below:

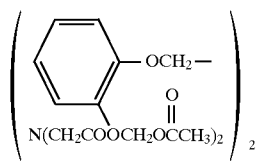

EXAMPLES

The present invention is demonstrated by in vitro and in vivo data. In FIG. 1, 20 μM BAPTA-AM were found to totally depress the regulatory volume decrease (RVD) that occurs following hyposmotic swelling of cultured human non-pigmented ciliary epithelial (NPE) cells. In this example, NPE cells were loaded in an isosmotic (290 mOsm) solution containing 20 μM BAPTA-AM for 30 minutes prior to suspension in a hyposmotoic (198 mOsm) solution. Control cells were subjected to the same hyposmotic solution but without prior loading with BAPTA. Changes in cell volume were measured using a Coulter Counter interfaced to a Coulter Channelyzer. It is noted that, following osmotic swelling, control cells regulate towards their original isosmotic volume while BAPTA-loaded cells remain swollen. The above findings indicate that intracellular BAPTA via chelation of $Ca^{2+}i$ inhibits solute and osmotically obliged $H_2O$ efflux. Because the $Ca^{2+}i$-dependent ion flux pathways activated following osmotic cell swelling of NPE cells are involved in aqueous secretion, BAPTA will inhibit aqueous humor formation and, thus, lower IOP.

Figure 2:
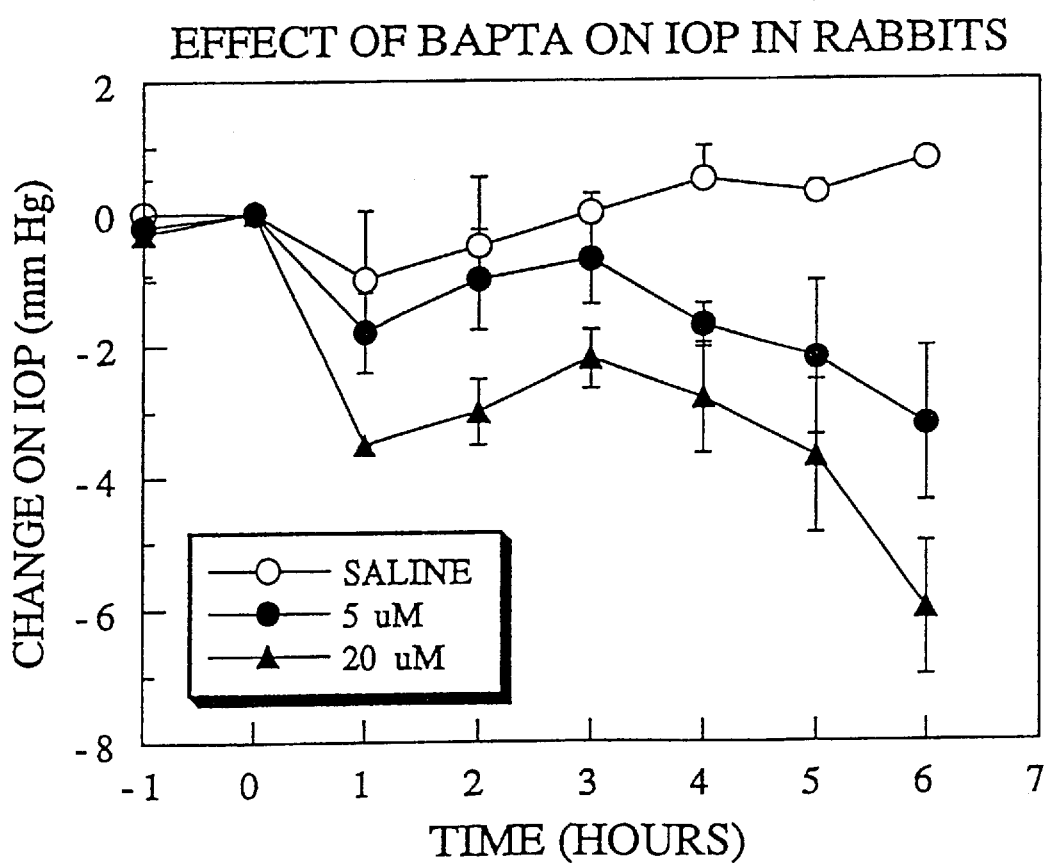
FIG. 2 is a graph showing the effect of intracameral administration of two dosages of the drug BAPTA-AM on the intraocular pressure (IOP) in the rabbit eye.
Figure 3:
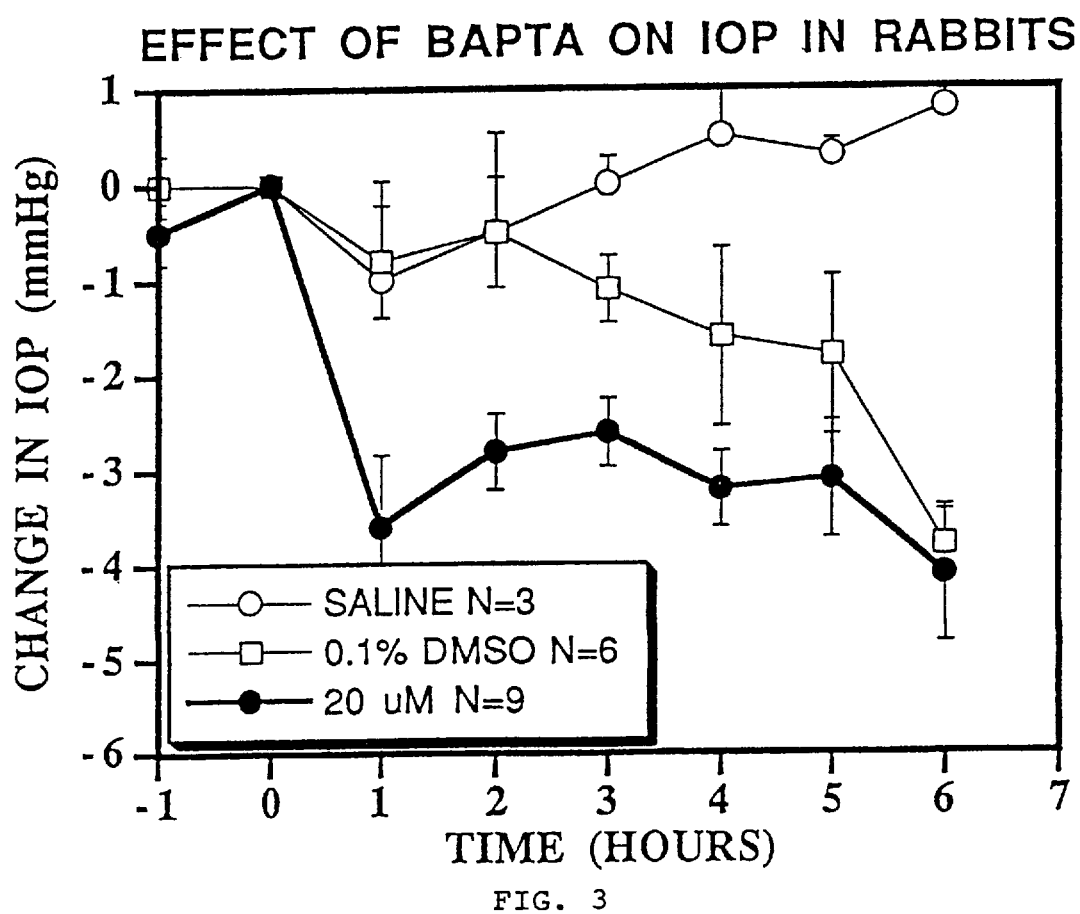
FIG. 3 is a graph showing the effect of intracameral administration of the drug BAPTA-AM, as compared to saline and dimethyl sulfoxide (DMSO) on the intraocular pressure (IOP) in the rabbit eye.

In the in vivo studies normotensive rabbits were injected intracamerally with 5 or 20 μM BAPTA-AM. FIGS. 2 and 3 shows that 20 μM BAPTA lowered IOP by 4 to 6 mm of Hg within 6 hours. Taken together the above in vitro and in vivo experiments demonstrate that chelation of $Ca^{2+}i$ in the ciliary epithelium will reduce IOP.

Several modifications of the present invention may become readily apparent to those skilled in the art in light of the present disclosure. For example, acetylcholine-like esters of BAPTA or other prodrugs of calcium chelating agents will provide target-specific activity for lowering IOP. In general since acetylchlorine esterases reside primarily in the ciliary body and retina, the acetylcholine ester of BAPTA or another calcium chelating agent should only be hydrolyzed in the above tissue/cell types.

The advantages of using acetylcholine esters of BAPTA or another calcium chelating agent are as follows: First, $Ca^{2+}i$ will only be chelated/buffered in the ciliary epithelium and retina. Thus, other ocular cell types will be left unperturbed. Second, extracellular $Ca^{2+}$ which is critical for maintaining tight junction integrity in fluid transporting epithelia will remain unaltered since the acetylcholine ester of BAPTA will not be appreciably hydrolyzed in the absence of esterases. Third, since the retina including retinal ganglion cells will also contain BAPTA in its ionized form, large increases in retinal ganglion cell $Ca^{2+}i$ will be prevented. Because increases in retinal and in particular optic nerve $Ca^{2+}i$ are believed to play a deleterious role in the pathophysiology of glaucoma and neural degeneration, intracellular BAPTA in the above cell types will afford an additional neuroprotective effect.

In view of the above, it is clear that the scope of the present invention should be interpreted solely on the basis of the following claims, as such claims are read in light of the disclosure.

What is claimed is:

1. A method for treating optical neuropathy associated with elevated ocular pressure in the eye of a mammal which comprises the step of administering to the mammal a pharmaceutical composition which comprises as its active ingredient one or more compounds having calcium chelating activity.

2. The method of claim 1 wherein the compound having calcium chelating activity is selected from the group consisting of compounds represented by the formula:

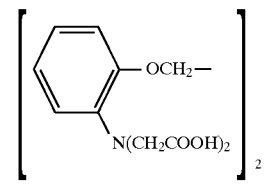

and lower alkyl and alkoxyalkyl esters thereof.

3. The method of claim 2 wherein the composition contains approximately 0.0001 to 0.1 per cent weight by volume of said compound having calcium chelating activity.

4. The method of claim 1 wherein the compound having calcium chelating activity is selected from the groups consisting of compounds represented by the formula:

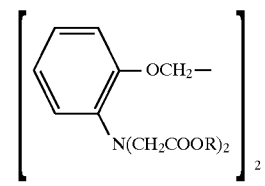

wherein R is selected from the group consisting of alkyl radicals having from 1 to 6 carbon atoms and

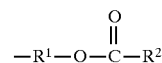

wherein $R^1$ is an alkylene radical having from 1 to 6 carbon atoms and $R^2$ is R and wherein R, $R^1$ and $R^2$ may be interrupted with O or N radicals.

5. The method of claim 4 wherein R is selected from the group consisting of

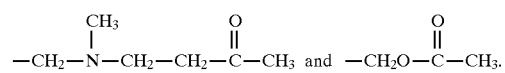

6. The method of claim 5 wherein R is

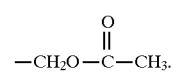

* * * * *

UNITED STATES PATENT AND TRADEMARK OFFICE
CERTIFICATE OF CORRECTION

PATENT NO. : 5,891,911  
DATED : April 6, 1999  
INVENTOR(S) : Adorante et al

Page 1 of 2

It is certified that error appears in the above-indentified patent and that said Letters Patent is hereby corrected as shown below:

On the title page: Item [22]

Delete "Jul. 28, 1995" and insert in place thereof --Jul. 28, 1994--

UNITED STATES PATENT AND TRADEMARK OFFICE
CERTIFICATE OF CORRECTION

PATENT NO. : 5,891,911
DATED : July 28, 1995
INVENTOR(S) : Adorante et al

It is certified that error appears in the above-identified patent and that said Letters Patent is hereby corrected as shown below:

IN THE DRAWINGS:

Figure 1, delete "0.9" and insert in place thereof --0.0--

Signed and Sealed this

Thirtieth Day of January, 2001

Attest:

Q. TODD DICKINSON

*Attesting Officer*     *Director of Patents and Trademarks*